US010725534B2

United States Patent
Son et al.

(10) Patent No.: US 10,725,534 B2
(45) Date of Patent: Jul. 28, 2020

(54) APPARATUS AND METHOD OF GENERATING MACHINE LEARNING-BASED CYBER SICKNESS PREDICTION MODEL FOR VIRTUAL REALITY CONTENT

(71) Applicant: ELECTRONICS AND TELECOMMUNICATIONS RESEARCH INSTITUTE, Daejeon (KR)

(72) Inventors: Wook Ho Son, Daejeon (KR); Seung Woo Nam, Daejeon (KR); Hee Seok Oh, Seoul (KR); Beom Ryeol Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 16/140,210

(22) Filed: Sep. 24, 2018

(65) Prior Publication Data

US 2019/0171280 A1 Jun. 6, 2019

(30) Foreign Application Priority Data

Dec. 5, 2017 (KR) .................... 10-2017-0166134

(51) Int. Cl.
*G06F 3/048* (2013.01)
*G06F 3/01* (2006.01)
(Continued)

(52) U.S. Cl.
CPC ............. *G06F 3/011* (2013.01); *G06F 3/048* (2013.01); *G06F 17/18* (2013.01); *G06N 20/00* (2019.01); *G06T 19/006* (2013.01); *G02B 27/017* (2013.01)

(58) Field of Classification Search
CPC .......... G06F 3/011; G06F 3/048; G06F 17/18; G06N 20/00; G06T 19/006; G02B 27/017
See application file for complete search history.

(56) References Cited

U.S. PATENT DOCUMENTS 7,128,705 B2 * 10/2006 Brendley .............. A61M 21/00
600/27
7,174,039 B2 * 2/2007 Koo ........................ G06T 15/20
382/154

(Continued)

FOREIGN PATENT DOCUMENTS

KR        10-1717379 B1    3/2017
KR    10-2017-0055135 A    5/2017

OTHER PUBLICATIONS

Y. H. Nam et al., "Automatic Detection of Nausea Using Bio-Signals During Immerging in a Virtual Reality Environment", Oct. 25, 2001, pp. 1-5.

*Primary Examiner* — Carolyn R Edwards

(57) ABSTRACT

Disclosed is an apparatus and method of generating a VR sickness prediction model. A method of generating a VR sickness prediction model according to the present disclosure includes: displaying virtual reality content on a display unit; detecting first VR sickness information of a user who experiences the virtual reality content using a sensor; determining second VR sickness information using a user input that is input from the user in response to a request for inputting a degree of VR sickness for the virtual reality content; performing machine learning based on supervised learning using VR sickness-inducing factors for the virtual reality content, the first VR sickness information, and the second VR sickness information; and determining a correlation between the VR sickness-inducing factors and a list of VR sickness symptoms on a basis of the performed machine learning.

10 Claims, 7 Drawing Sheets

(51) Int. Cl.
    *G06T 19/00*     (2011.01)
    *G06F 17/18*     (2006.01)
    *G06N 20/00*     (2019.01)
    *G02B 27/01*     (2006.01)

(56) References Cited

U.S. PATENT DOCUMENTS

| | | | |
|---|---|---|---|
| 9,999,835 B2* | 6/2018 | Watson | G06F 3/013 |
| 10,275,918 B2* | 4/2019 | Appakutty | G01P 15/14 |
| 2012/0050325 A1* | 3/2012 | Joo | A63F 13/65 |
| | | | 345/633 |
| 2016/0228771 A1* | 8/2016 | Watson | G06F 3/013 |
| 2016/0246057 A1* | 8/2016 | Hasegawa | G02B 27/017 |
| 2017/0255258 A1* | 9/2017 | Feiner | G02B 27/0093 |
| 2017/0358141 A1* | 12/2017 | Stafford | G06F 3/011 |
| 2018/0096517 A1* | 4/2018 | Mallinson | A61B 5/04884 |
| 2019/0114841 A1* | 4/2019 | Sato | G06T 19/20 |
| 2019/0172264 A1* | 6/2019 | Oh | G06T 19/006 |

\* cited by examiner

[FIG. 1]
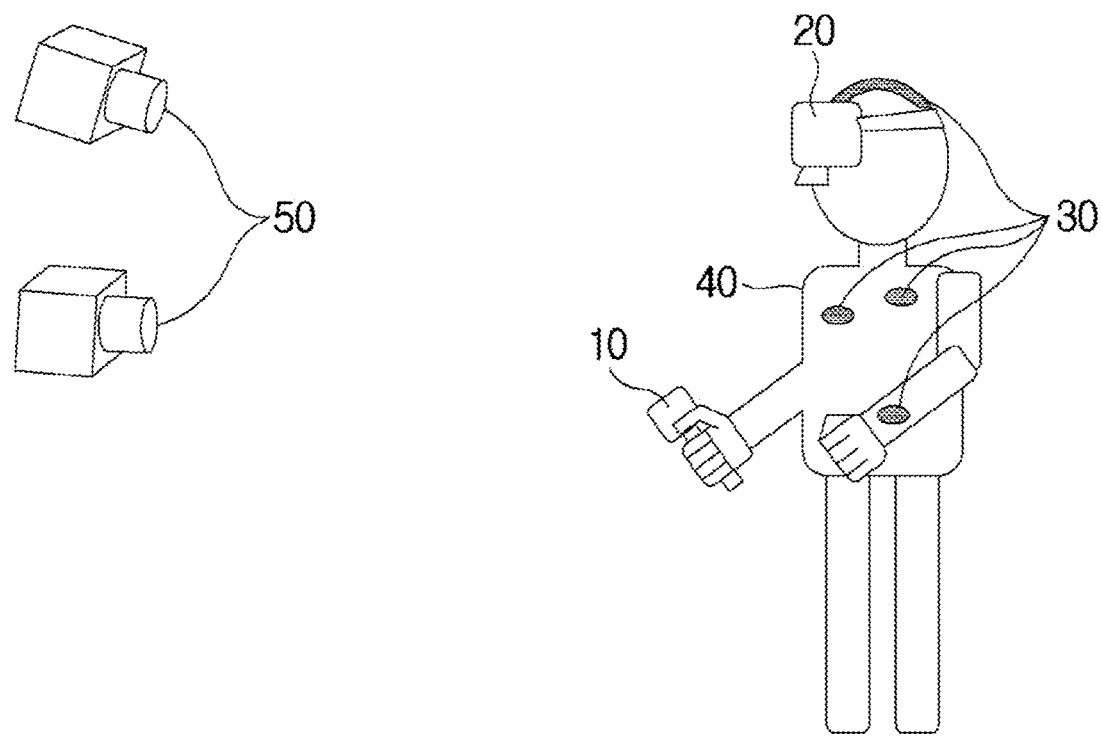

[FIG. 2]
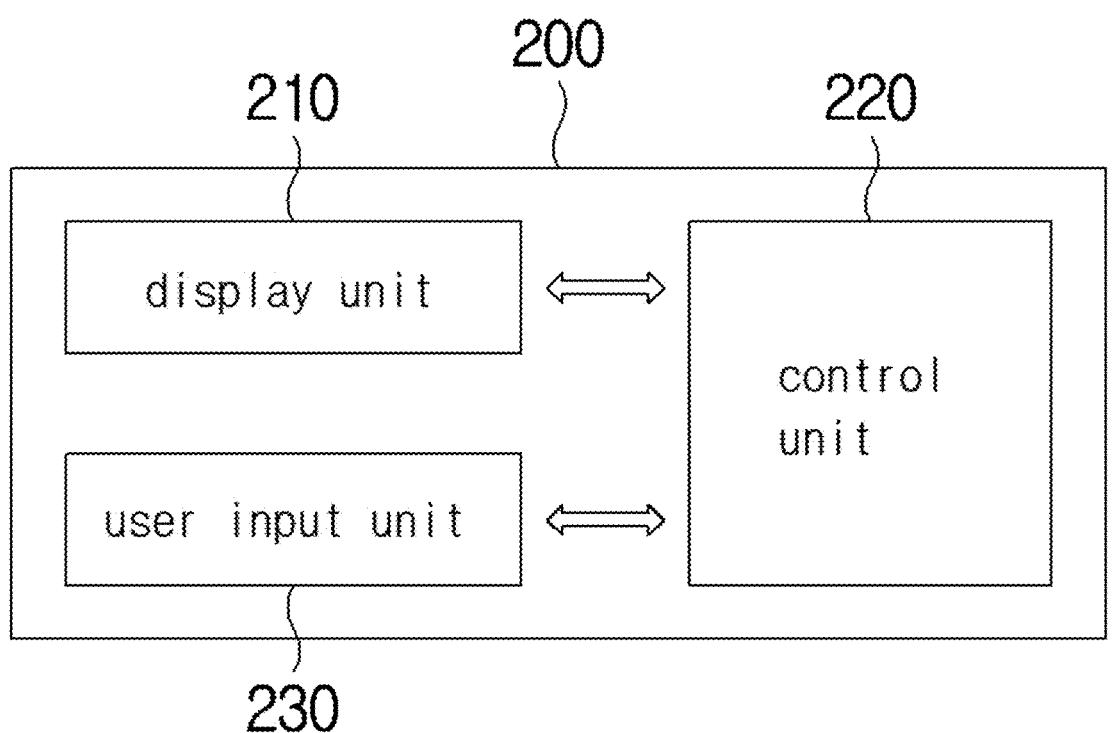

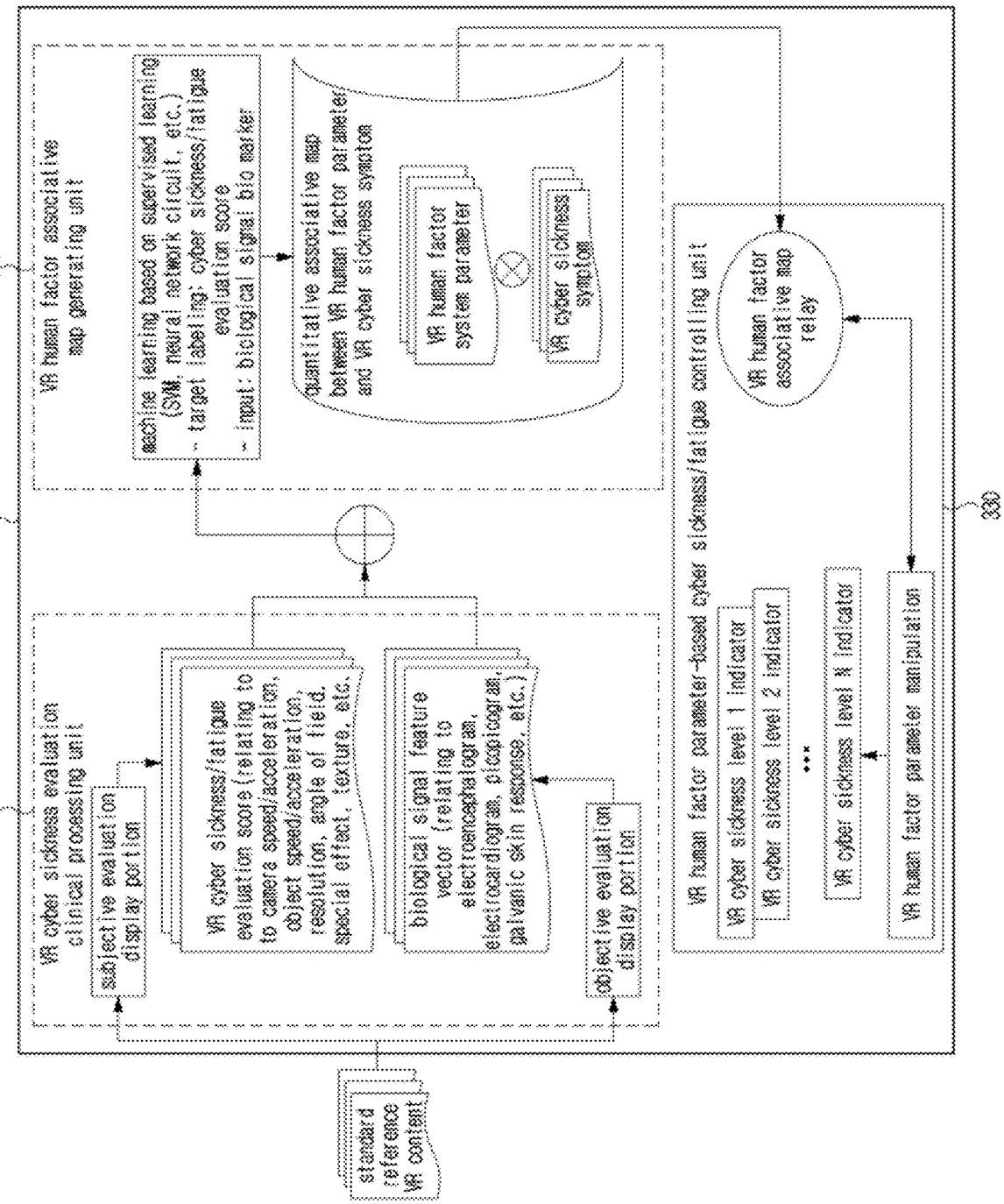
[ FIG. 3 ]

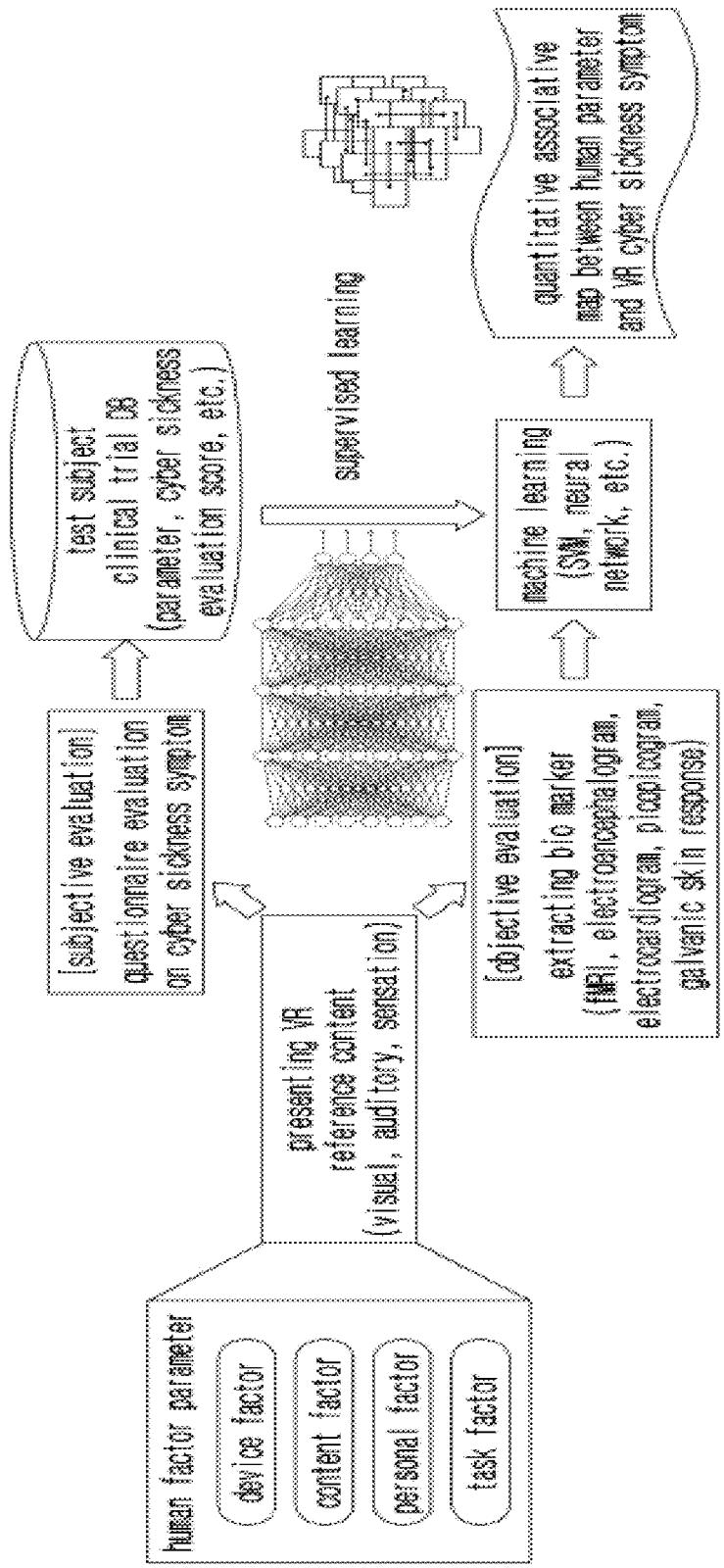
[FIG. 4]

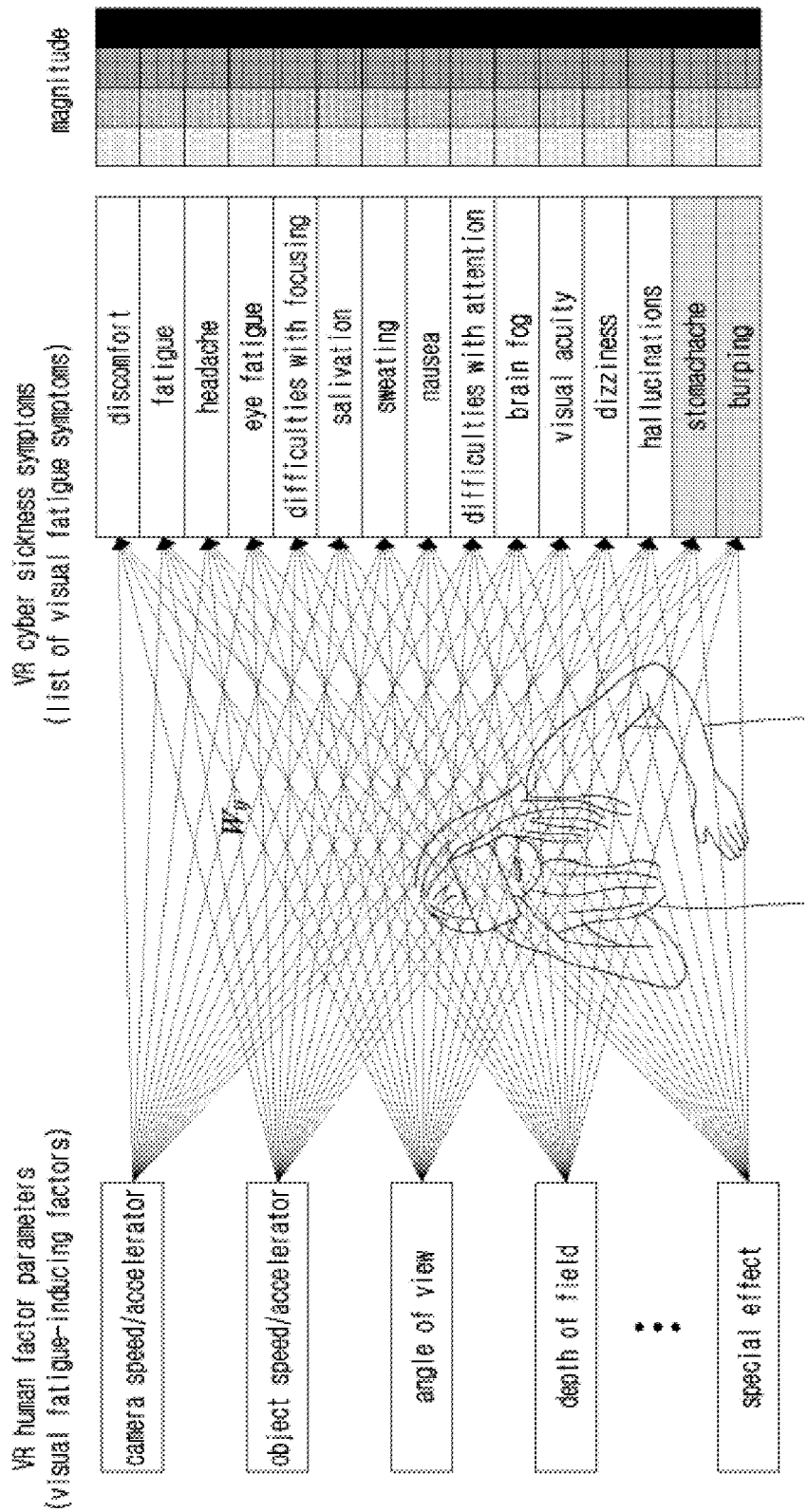
[ FIG. 5 ]

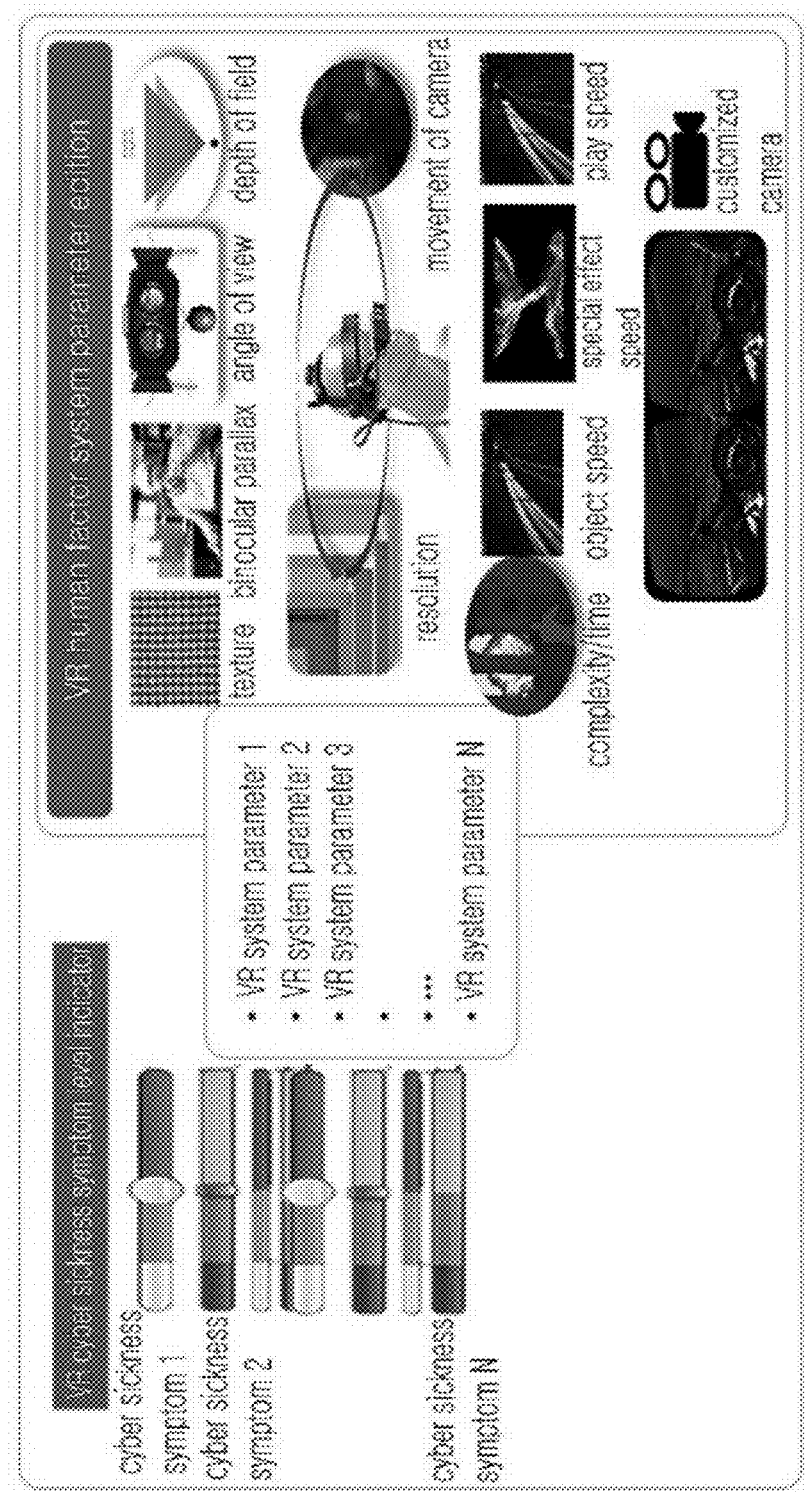
[ FIG. 6 ]

[FIG. 7]
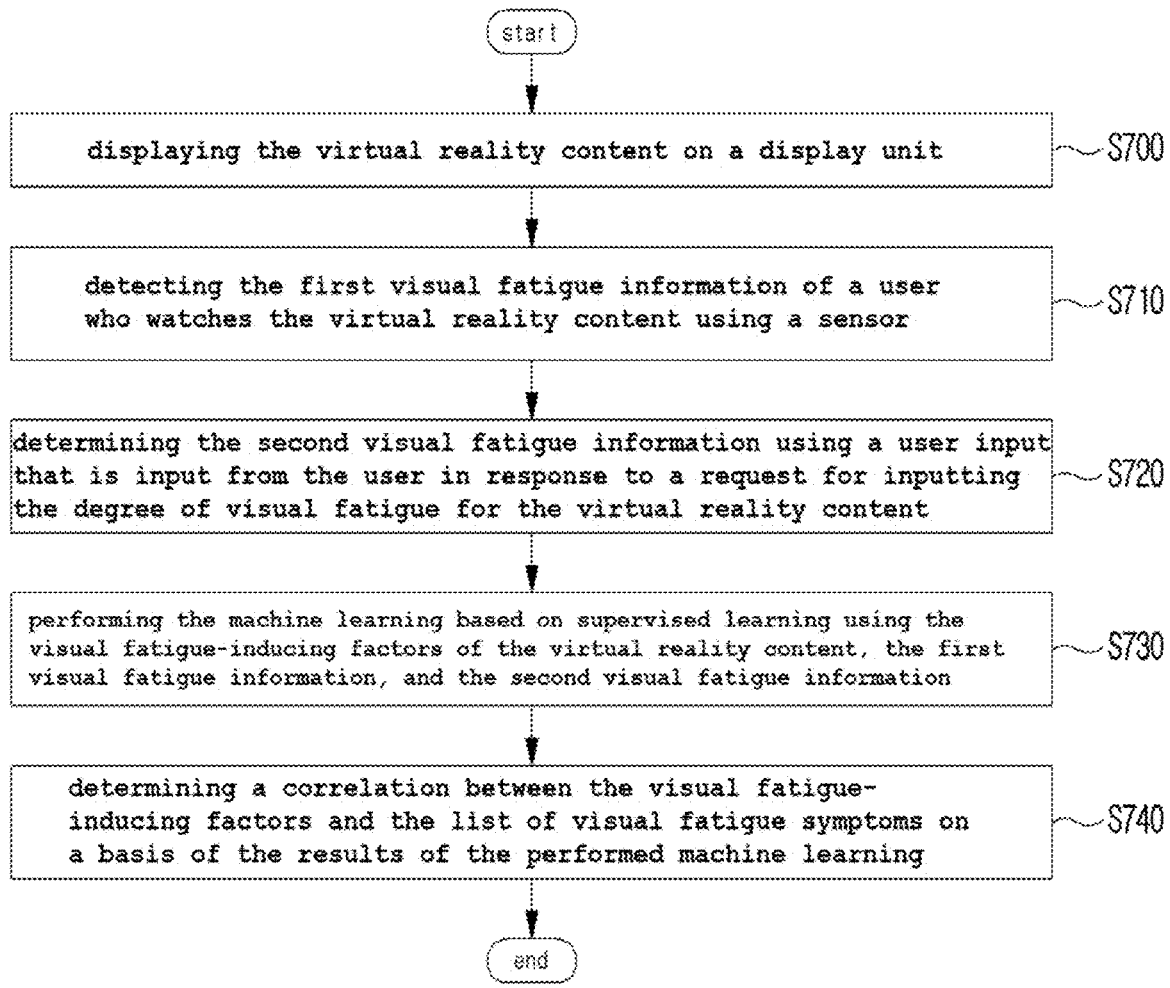

APPARATUS AND METHOD OF GENERATING MACHINE LEARNING-BASED CYBER SICKNESS PREDICTION MODEL FOR VIRTUAL REALITY CONTENT

CROSS REFERENCE TO RELATED APPLICATION

The present application claims priority to Korean Patent Application No. 10-2017-0166134, filed Dec. 5, 2017, the entire contents of which is incorporated herein for all purposes by this reference.

BACKGROUND OF THE INVENTION

Field of the Invention

The present disclosure relates generally to an apparatus and a method of generating a machine learning-based VR (Virtual Reality) sickness (or motion sickness) prediction model for virtual reality content. More particularly, the present disclosure relates to an apparatus and a method of generating a correlation model between VR sickness inducing-factors for virtual reality content and VR sickness for virtual reality content by performing machine learning based on supervised learning, and quantitatively adjusting the VR sickness based on the generated correlation model.

Description of the Related Art

VR technology is a high technology that dynamically reproduces, through a virtual environment, a real situation which is accompanied with cost, time, or risk in order to construct a real environment. The VR technology has various applications, such as being used for purposes of training in various application fields of national defense, medical, production, etc., or being applied to entertainment fields such as games, theme parks, and movies. In recent years, as head-mounted displays (HMDs) have become widespread in popularity, the availability of virtual reality technology is increasing. In order to improve the market performance and practical use of such virtual reality technology, it is necessary to solve VR sickness such as cyber sickness which may be caused to the user who experiences virtual reality content and thus ensures long-term usability.

In order to avoid cyber sickness, a feeling of fatigue, and the like that may occur when experiencing a video through the VR HMD, the VR latency time should be fundamentally reduced. In general, when the VR latency time is less than 20 ms, it is experimentally/theoretically known that the VR sickness is alleviated considerably. The VR latency time consists of head tracking information processing time and VR image rendering time in a case of PC based VR HMD, and latency time due to transmission of network should also be considered in a case of a mobile type such as a mobile phone. Specifically, the HMD head tracking depends on hardware and the performance thereof is determined for each product used. The VR rendering depends on system specifications and the complexity of the virtual environment.

In addition, the intrinsic characteristics of the VR HMD image content are known to have a great influence on the VR sickness in addition to the VR latency time. Specifically, the characteristics may be determined by various system parameters such as a movement of a camera, movement of graphic object, resolution, field of view, binocular disparity, special effects, and the like.

On the other hand, a methodology of evaluating the degree of VR sickness caused by experiencing VR content is based on a questionnaire survey for identifying the cause of a feeling of fatigue and a fatigue evaluation based on a biological signal measurement with respect to the existing 3D stereo images. Specifically, the objective evaluation method based on the biological signal measurement or the like is a method of analyzing a change occurring in a user by sensing a signal generated from the user continuously before and after experiencing the VR content, as well as during experiencing the VR content. On the other hand, the subjective method using the questionnaire survey is a method including a preliminary questionnaire survey before being visually stimulated by the VR content and a VR sickness survey for the VR content after experiencing the VR content and completing the experience thereof. However, conventional methodology for identifying the cause of the a feeling of fatigue for the VR image is based on the fact that a qualitative correlation between the result obtained by the clinical experiment and the feeling of fatigue for the VR image is relatively analyzed using statistical numerals (for example, ANOVA analysis), whereby it is used only as an indirect reference material for realizing a function of controlling VR cyber sickness and fatigue-inducing degree that is required for developing VR applications in a real industrial field. However, in order to secure marketability and popularity of VR applications developed in various fields such as games, theme parks, advertisements, movies, defense simulation, virtual medicine, and virtual manufacturing, a method of reducing the VR cyber sickness and the feeling of fatigue is required. For this purpose, the various factors involved in inducing the VR cyber sickness and the feeling of fatigue have to be accurately adjusted on a basis of cognitive/neurological support and clinical grounds.

Recently, artificial intelligence and machine learning technology come into the spotlight. The machine learning means learning by computer using data, and machine learning algorithms are greatly classified into supervised learning, unsupervised learning, and reinforcement learning. In particular, the supervised learning is a method of learning by system in a state that a label, that is, an explicit correct answer is tagged to the data. Specifically, learning is performed in a form of 'a set of data and label', and when the learning is completed with the constructed set of test data, it is possible to measure how accurately an unlabeled set of test data is predicted by the learned algorithm.

SUMMARY OF THE INVENTION

It is an object of the present disclosure to provide to an apparatus and a method of quantitatively analyzing a correlation between VR sickness-inducing factors and VR sickness of a user who experiences virtual reality content through a video display device such as HMD using machine learning.

The technical objects to be achieved by the present disclosure are not limited to the technical matters mentioned above, and other technical subjects that are not mentioned are to be clearly understood by those skilled in the art from the following description.

In order to achieve the above object, according to one aspect of the present invention, there is provided a method of generating a VR sickness prediction model, the method comprising: displaying virtual reality content on a display unit; detecting first VR sickness information of a user who experiences the virtual reality content using a sensor; determining second VR sickness information using a user input that is input from the user in response to a request for inputting a degree of VR sickness for the virtual reality content; performing machine learning based on supervised learning using VR sickness-inducing factors for the virtual reality content, the first VR sickness information, and the second VR sickness information; and determining a correlation between the VR sickness-inducing factors and a list of VR sickness symptoms on a basis of the performed machine learning.

According to another aspect of the present disclosure, there is provided an apparatus for generating a VR sickness prediction model, the apparatus comprising: a display unit displaying virtual reality content; a user input unit; and a control unit detecting first VR sickness information of a user who experiences the virtual reality content using a sensor, determining second VR sickness information using a user input that is input from the user in response to a request for inputting a degree of VR sickness for the virtual reality content, performing machine learning based on supervised learning using VR sickness-inducing factors for the virtual reality content, the first VR sickness information, and the second VR sickness information, and determining a correlation between the VR sickness-inducing factors and a list of VR sickness symptoms on a basis of the performed machine learning.

It is to be understood that the foregoing summarized features are exemplary aspects of the following detailed description of the present invention without limiting the scope of the present invention.

According to this disclosure, it is possible to provide to an apparatus and a method of quantitatively analyzing using machine learning a correlation between VR sickness-inducing factors and VR sickness of a user who experiences virtual reality content through a video display device such as HMD.

In addition, according to this disclosure, the virtual reality cyber sickness/feeling of fatigue can be quantitatively controlled in advance when manufacturing the virtual reality application content using correlation between the VR sickness-inducing factors of virtual reality content and the VR sickness of the user.

The effects obtainable from the present disclosure are not limited to the effects mentioned above, and it will be clearly appreciated that other effects not mentioned can be clearly understood by those skilled in the art from the description below.

BRIEF DESCRIPTION OF THE DRAWINGS

The above and other objects, features and other advantages of the present invention will be more clearly understood from the following detailed description when taken in conjunction with the accompanying drawings, in which:

FIG. 1 is a diagram illustrating a system for acquiring VR sickness information for virtual reality content using a sensor and a user input according to an embodiment;

FIGS. 2 and 3 are block diagrams illustrating a configuration of an apparatus for generating a machine learning-based VR sickness prediction model for virtual reality content according to an embodiment;

FIGS. 4 and 5 are diagrams illustrating a process of determining a correlation between VR sickness-inducing factors and a list of VR sickness symptoms by performing machine learning according to an embodiment;

FIG. 6 is a diagram illustrating an example in which a correlation between VR sickness-inducing factors and a list of VR sickness symptoms according to an embodiment is displayed using a graphical user interface; and FIG. 7 is a flowchart illustrating an operation method of an apparatus for generating a machine learning-based VR sickness prediction model for virtual reality content according to an embodiment.

DETAILED DESCRIPTION OF THE INVENTION

Hereinbelow, exemplary embodiments of the present disclosure will be described in detail such that the ordinarily skilled in the art would easily understand and implement an apparatus and a method provided by the present disclosure in conjunction with the accompanying drawings. However, the present disclosure may be embodied in various forms and the scope of the present disclosure should not be construed as being limited to the exemplary embodiments.

In describing embodiments of the present disclosure, well-known functions or constructions will not be described in detail when they may obscure the spirit of the present disclosure. Further, parts not related to description of the present disclosure are not shown in the drawings and like reference numerals are given to like components.

In the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure.

In the present disclosure, all of the constituent elements described in various embodiments should not be construed as being essential elements but some of the constituent elements may be optional elements. Accordingly, embodiments configured by respective subsets of constituent elements in a certain embodiment also may fall within the scope of the present disclosure. In addition, embodiments configured by adding one or more elements to various elements also may fall within the scope of the present disclosure.

Hereinbelow, exemplary embodiments of the present disclosure will be described in detail with reference to the accompanying drawings. Throughout the drawings, the same reference numerals will refer to the same or like parts.

FIG. 1 is a diagram illustrating a system for obtaining VR sickness information for virtual reality content using a sensor and a user input according to an embodiment.

An apparatus for generating a machine learning-based VR sickness prediction model for virtual reality content according to an embodiment is capable of displaying virtual reality content on a display unit, detecting first VR sickness information of a user who experiences the virtual reality content using a sensor, and determining second VR sickness using a user input inputted from the user in response to a request for inputting a degree of the VR sickness for the virtual reality content.

A sensor according to an embodiment may include an image capturing sensor (or observation type sensor) or a biological signal detection sensor (or a wearable sensor).

Referring to FIG. 1, when a user 40 wearing a video display device 20 such as a head mounted display (HMD) is experiencing virtual reality content displayed on the video display device 20, the apparatus for generating a machine learning-based VR sickness prediction model for virtual reality content may track changes in the posture, the state, the pupils, the facial expression, the gesture, and the voice of the user 40 using the observation type sensor 50. According to an embodiment, the observation type sensor 50 may include, but is not limited to, an MRI, an FMRI, an image sensor, an infrared sensor, and the like, and may include a sensor that is capable of tracking a user's motion. In addition, the apparatus for generating a machine learning-based VR sickness prediction model for virtual reality content includes a sensor capable of detecting a biological signal such as an electroencephalogram EEG, an electrocardiogram ECG, picopicogram PPG, galvanic skin response GSR, and a vomiting measurement of a user 40 using a wearable sensor 30. The user's image acquired from the image capturing sensor or the magnitude of the user's biological signal obtained from the biological signal detection sensor may be referred to as the first VR sickness information (or objective VR sickness information). Also, according to an embodiment, the apparatus for generating a VR sickness prediction model may acquire a feature vector for performing machine learning based on the first VR sickness information, in which the feature vector form may be generated by extracting the first VR sickness information on the time axis.

Also, the apparatus for generating a VR sickness prediction model for virtual reality content may receive a degree of VR sickness from the user in response to a request for inputting the degree of the VR sickness for the virtual reality content before/after or during providing (or exposing) the virtual reality content to the user. The request for inputting the degree of the VR sickness for the virtual reality content according to an embodiment may be issued to the user at a predetermined time interval. In addition, the user input according to an embodiment may be an input through a user interface displayed on the display unit or an input from an input device provided in the apparatus for generating a VR sickness prediction model. In addition, the virtual reality content according to an embodiment may be a set of a plurality of individual virtual reality contents in which each value of VR sickness-inducing factors is controlled. On the other hand, the information acquired from the user in response to the request for inputting the degree of the VR sickness for the virtual reality content is referred to as the second VR sickness information (or subjective VR sickness information), which will be described later.

According to an embodiment, the apparatus for generating a VR sickness prediction model is capable of performing machine learning based on supervised learning using the VR sickness-inducing factors, the first VR sickness information, and the second VR sickness information of the virtual reality content, and determining a correlation between the VR sickness-inducing factors and the list of VR sickness symptoms on a basis of the results of the performed machine learning. For example, the apparatus for generating the VR sickness prediction model may determine quantitative correlation between the VR sickness-inducing factors and the list of VR sickness symptoms, by causing the items in the list of VR sickness symptoms to be gradually changed in magnitude as the VR sickness-inducing factors for the virtual reality content change.

According to an embodiment, the VR sickness-inducing factors (or VR human factor parameters) may include, but are not limited to, movement of a camera, movement of an object, playback information, resolution, binocular parallax, depth of field, angle of view, image feature, special effect, and texture effect, and may further include factors capable of inducing VR sickness such as cyber sickness to a user who experiences the virtual reality content, such as a change in intrinsic characteristics of the content or extrinsic characteristics of the content (for example, movement of an object, movement of a camera).

According to an embodiment, the list of the user's VR sickness symptoms (or VR cyber sickness symptoms) for the virtual reality content is information including the items in the list of VR sickness symptoms and the magnitude of each item with respect to the corresponding user and virtual reality content, in which items in the list of VR sickness symptoms according to the embodiments may include, but are not limited to, discomfort, fatigue, headache, eye fatigue, difficulties with focusing, sweating, nausea, difficulties with attention, brain fog, visual acuity, dizziness, hallucinations, stomachache, cyber sickness, burping, or other symptoms, and may further include specific symptoms that may be caused by experiencing the virtual reality content.

Meanwhile, the second VR sickness information according to an embodiment may be the degree of the items in the list of VR sickness symptoms input from the user in response to a request for inputting the degree of the VR sickness for the virtual reality content. For example, the apparatus for generating a VR sickness prediction model may acquire the degree for each of items of headache, nausea, and dizziness input from the user in response to the request for inputting the degree of the VR sickness while experiencing the virtual reality content called A. In addition, the second VR sickness information according to an embodiment may be input through a user interface displayed on a display unit, input from an input device provided in the apparatus for generating a VR sickness prediction model, or acquired using the result of writing a simulation sickness questionnaire. According to an embodiment, the input device provided in the apparatus for generating the VR sickness prediction model may be a user interface tool such as a controller, but is not limited thereto.

On the other hand, the apparatus for generating the VR sickness prediction model according to an embodiment determines a feature vector acquired using the first VR sickness information as data in the machine learning based on supervised learning, determine the second VR sickness information as a label for the data in the machine learning based on supervised learning, and perform the machine learning based on supervised learning using the data and the label for the data. In addition, the apparatus for generating the VR sickness prediction model according to an embodiment may predict a correlation between the VR sickness-inducing factors and the list of VR sickness symptoms for any virtual reality content on a basis of the machine learning result.

FIGS. 2 and 3 are block diagrams illustrating a configuration of an apparatus for generating a machine learning-based VR sickness prediction model for virtual reality content (hereinafter, simply referred to as "a VR sickness prediction model generating apparatus") according to an embodiment.

Referring to FIG. 2, the VR sickness prediction model generating apparatus 200 according to an embodiment includes a display unit 210, a control unit 220, and a user input unit 230. It should be noted, however, that this is only illustrative of some of the components necessary for explaining the present embodiment, and components included in the VR sickness prediction model generating apparatus 200 are not limited to the examples described above.

For example, referring to FIG. 3, the VR sickness prediction model generating apparatus 300 further includes a VR cyber sickness evaluation clinical processing unit 310, VR human factor associative map generating unit 320, and a VR human factor parameter-based cyber sickness/fatigue controlling unit 330. The VR sickness prediction model generating apparatus 300 in FIG. 3 corresponds to the VR sickness prediction model generating apparatus 200 in FIG. 2.

Referring to FIG. 2, the display unit 210 converts a video signal, a data signal, an OSD signal, and a control signal processed in the control unit 220 to generate a driving signal. The display unit 210 may display content (e.g., moving picture) input through a communication unit or an input/output unit. The display unit 210 also outputs image stored in a storage unit under the control of the control unit 220. In addition, the display unit 210 displays a voice user interface UI (for example, including voice command guide) for performing voice recognition task corresponding to voice recognition or motion user interface UI (for example, including user motion guide for motion recognition) for performing motion recognition task corresponding to motion recognition. Also, the display unit 210 may display and output information processed by the VR sickness prediction model generating apparatus 200. For example, the display unit 210 may display a virtual image, a user interface for selecting the virtual image, or a user interface for setting an operation of the virtual image. The display unit 210 may also display information processed in an HMD device or an external immersive virtual reality imaging device.

The display unit 210 according to an embodiment displays the virtual reality content. Further, the display unit 210 according to an embodiment may display, using a graphical user interface GUI, a correlation between the VR sickness-inducing factors and the list of VR sickness symptoms for the virtual reality content determined by performing the machine learning.

The control unit 220 performs a function of controlling the overall operation of the VR sickness prediction model generating apparatus 200 and the signal flow between the internal components of the VR sickness prediction model generating apparatus 200 for the virtual reality content and a function of processing data. The control unit 220 may execute various applications stored in the storage unit when an input is performed by the user or a predefined condition is satisfied. The control unit 220 of FIG. 2 may include the VR cyber sickness evaluation processing unit 310, the VR human factor associative map generating unit 320, and the VR human factor parameter-based cyber sickness/fatigue controlling unit 330 in FIG. 3. However, only partial components necessary for explaining the present embodiment are shown, and the components included in the control unit 220 are not limited to the above-described examples.

The control unit 220 according to an embodiment: detects the first VR sickness information of a user who experiences the virtual reality content using a sensor and generates a user input unit 230; determines the second VR sickness information using a user input that is input to the user input unit 230 in response to a request for inputting a degree of VR sickness for the virtual reality content; performs the machine learning based on supervised learning using the VR sickness-inducing factors of the virtual reality content, the first VR sickness information, and the second VR sickness information; and determines a correlation between the VR sickness-inducing factors and the list of VR sickness symptoms on a basis of the result of the performed machine learning.

Further, the control unit 220 according to an embodiment causes items in the list of VR sickness symptoms to be changed in magnitude as the VR sickness-inducing factors of the virtual reality content change.

In addition, the control unit 220 according to an embodiment determines the feature vector acquired using the first VR sickness information as data in the machine learning based on supervised learning; determines the second VR sickness information as a label for the data in the machine learning based on supervised learning; and performs the machine learning based on supervised learning using the data and the label for the data. In addition, the control unit 220 according to an embodiment predicts the correlation between the VR sickness-inducing factors and the list of VR sickness symptoms for any virtual reality content on a basis of the result of the machine learning.

The user input unit 230 is defined as a means for a user to input data for controlling the VR sickness prediction model generating apparatus 200 for the virtual reality content. For example, the user input unit 230 may include, but is not limited to, a keypad, a dome switch, a touchpad (contact capacitance method, pressure resistive membrane method, infrared sensing method, surface ultrasonic conductive method, integral tension measuring method, piezo effect method, etc.), a jog wheel, a jog switch, and the like.

The user input unit 230 according to an embodiment may receive a user input in response to a request for inputting a degree of VR sickness for the virtual reality content. The user input may also be input through a user interface displayed on the display unit 210 or input from an input device provided on the VR sickness prediction model generating apparatus 200. According to an embodiment, the input device provided in the VR sickness prediction model generating apparatus 200 may be a user interface tool such as a controller, but is not limited thereto.

As will be described below, the operation of the VR sickness prediction model generating apparatus 300 based on machine learning for the virtual reality content will be described with reference to FIGS. 3 to 6.

The VR sickness prediction model generating apparatus 300 according to an embodiment includes the cyber sickness evaluation clinical processing unit 310, the VR human factor associative map generating unit 320, and the VR human factor parameter-based cyber sickness/fatigue controlling unit 330.

The cyber sickness evaluation clinical processing unit 310 according to an embodiment builds a table form database (DB) of the results obtained by performing VR cyber sickness/fatigue evaluation on a plurality of users using reference VR content. Specifically, referring to FIG. 3, the VR cyber sickness evaluation clinical processing unit 310 may build a table form database of a relationship between the VR human factor parameter (or VR sickness-inducing factors) and the VR cyber sickness evaluation score (or the second VR sickness information), by using a biological signal measurement/analysis result (objective evaluation display portion in FIG. 3) of a user who experiences the standard reference VR content for performing the VR cyber sickness/fatigue evaluation through a video display device such as a VR HMD device, and a result of questionnaire survey (subjective evaluation display portion in FIG. 3) input from the user in response to a request for inputting a degree of the VR sickness.

In addition, the VR human factor associative map generating unit 320 according to an embodiment determines a correlation between the VR human factor parameters (or VR sickness-inducing factors) and the VR fatigue symptoms (or a list of VR sickness symptoms) by applying mathematical analysis (e.g., statistical processing, machine learning) to the VR clinical trial database built from the VR cyber sickness evaluation clinical processing unit 310. Specifically, referring to FIGS. 3 and 4, the VR human factor associative map generating unit 320 performs the machine learning based on supervised learning on the VR clinical trial database built from the cyber sickness evaluation clinical processing unit 310 using mathematical correlation analysis method such as SVM or neural network circuit, in which feature vector acquired using the information (i.e., first VR sickness information) through the sensor is used as data in the machine learning based on supervised learning, and the result (i.e., the second VR sickness information) acquired from the subjective evaluation is used as a label for the data in the machine learning based on supervised learning. According to an embodiment, when performing the machine learning based on supervised learning, by tuning intrinsic parameters, the result of the individual correlation analysis of each VR human factor parameter (or VR sickness-inducing factor) and each VR cyber sickness symptoms (or each item in the list of VR sickness symptoms) is expressed as a normalized weight Wij between 0 and 1, and the overall result is expressed in the form of a weighted associative map, whereby the results may be stored in a matrix-like data structure. FIG. 5 is a diagram illustrating a process of determining a correlation between VR sickness-inducing factors and the list of VR sickness symptoms by performing machine learning according to an embodiment. Referring to FIG. 5, it is confirmed that the correspondence of each item in the list of VR sickness symptoms to each VR sickness-inducing factor and the magnitude of each item in the list of VR sickness symptoms are acquired, as a result of performing the machine learning.

In addition, the VR human factor parameter-based cyber sickness/fatigue controlling unit 330 according to an embodiment intuitively controls VR human factor parameters (or VR sickness-inducing factors) on GUI and adjusts in such a manner as to quantitatively level the VR cyber sickness symptoms (or the list of VR sickness symptoms) by level, using the VR human factor associative map determined from the VR human factor associative map generating unit 320. Specifically, referring to FIGS. 3 and 6, the VR human factor parameter-based cyber sickness/fatigue controlling unit 330 includes a VR human factor associative map relay, VR cyber sickness symptom level indicators of n (e.g., n is the number of items in the list of VR sickness symptoms), and a VR human factor parameter operator, in which the VR human factor parameter operator according to an embodiment intuitively operates the VR human factor parameters on GUI and assigns attributes thereto, and the VR human factor associative map relay according to an embodiment processes in such a manner as to relay a quantitative display function of each VR cyber sickness symptom level indicator corresponding to the VR human factor parameter operator. Referring to FIG. 6, it is confirmed that the correlation between the VR human factor parameters (or VR sickness-inducing factors) and the VR cyber sickness symptoms (or the list of VR sickness symptoms) is displayed on the display unit using the GUI.

FIG. 7 is a flowchart illustrating an operation method of an apparatus for generating a machine learning-based VR sickness prediction model for virtual reality content according to an embodiment.

In step S700, the VR sickness prediction model generating apparatus displays the virtual reality content on a display unit.

The VR sickness prediction model generating apparatus according to an embodiment displays a virtual image, a user interface for selecting the virtual image, and a user interface for setting an operation of the virtual image on the display unit. Also, the VR sickness prediction model generating apparatus displays information processed in an HMD device or an external immersive virtual reality imaging device.

In step S710, the VR sickness prediction model generating apparatus detects the first VR sickness information of a user who experiences the virtual reality content using a sensor.

The first VR sickness information according to an embodiment may be an image of a user acquired from an image capturing sensor or the magnitude of biological signal of the user acquired from a biological signal detection sensor.

In step S720, the VR sickness prediction model generating apparatus determines the second VR sickness information using a user input that is input from the user in response to a request for inputting the degree of VR sickness for the virtual reality content.

The request for inputting the VR sickness according to an embodiment is issued to the user at a predetermined time interval, in which the user input according to an embodiment may be an input through a user interface displayed on the display unit or an input from the input device provided in the VR sickness prediction model generating apparatus.

The second VR sickness information according to an embodiment is a degree of items in the list of VR sickness symptoms input from the user in response to the request for inputting the degree of VR sickness for the virtual reality content, in which the items in the list of VR sickness symptoms according to an embodiment may include, but not limited to, discomfort, fatigue, headache, eye fatigue, difficulties with focusing, sweating, nausea, difficulties with attention, brain fog, visual acuity, dizziness, hallucinations, stomachache, cyber sickness, burping, or other symptoms, and may further include specific symptoms that may be caused by experiencing the virtual reality content.

In step S730, the VR sickness prediction model generating apparatus performs the machine learning based on supervised learning using the VR sickness-inducing factors of the virtual reality content, the first VR sickness information detected in the step S710, and the second VR sickness information determined in the step S720.

The VR sickness-inducing factors (or VR human factor parameters) according to an embodiment may include, but are not limited to, movement of a camera, movement of an object, playback information, resolution, binocular parallax, depth of field, angle of view, image feature, special effect, or texture effect, and may further include factors capable of inducing VR sickness such as cyber sickness to a user who experiences the virtual reality content, such as a change in intrinsic characteristics of the content or extrinsic characteristics of the content (for example, movement of an object, movement of a camera).

In addition, the VR sickness prediction model generating apparatus according to an embodiment determines the feature vector acquired using the first VR sickness information as data in the machine learning based on supervised learning, determines the second VR sickness information as a label for the data in the machine learning based on supervised learning, and performs the machine learning based on supervised learning using the data and the label for the data.

In step S740, the VR sickness prediction model generating apparatus determines a correlation between the VR sickness-inducing factors and the list of VR sickness symptoms on a basis of the results of the performed machine learning in the step S730.

The VR sickness prediction model generating apparatus according to an embodiment may cause items in the list of VR sickness symptoms to be changed in magnitude as the VR sickness-inducing factors for the virtual reality content change.

In addition, the apparatus for generating VR sickness prediction model according to an embodiment may predict a correlation between the VR sickness-inducing factors and the list of VR sickness symptoms for any virtual reality content, on a basis of the results of machine learning.

In addition, the VR sickness prediction model generating apparatus according to an embodiment may determine the list of user's VR sickness symptoms for the virtual reality content on a basis of the first VR sickness information and the second VR sickness information, in which, for example, the VR sickness prediction model generating apparatus may determine the magnitudes of items in the list of VR sickness symptoms, by applying a given weight acquired using the first VR sickness information to a degree of at least one of items in the list of VR sickness symptoms acquired from the second VR sickness information Referring to FIGS. 1 to 7, an operation method of the VR sickness prediction model generating apparatus for virtual reality content according to an embodiment of this disclosure has been described above.

According to this disclosure, it is possible to provide an apparatus and method of quantitatively analyzing the correlation between the VR sickness-inducing factors and the VR sickness of the user who experiences the virtual reality content through a video display device such as an HMD, using the machine learning.

In addition, according to this disclosure, the virtual reality cyber sickness/fatigue may be quantitatively controlled in advance using the correlation between the VR sickness-inducing factors of virtual reality content and the user's VR sickness, when manufacturing the virtual reality application content.

In addition, according to this disclosure, it is possible to quantitatively control the cyber sickness/fatigue for VR contents in addition to simply analyzing the degree of cyber sickness due to the existing VR content through subjective questionnaire evaluation and observation of change in biological signal.

In addition, according to this disclosure, the database may be built through the VR cyber sickness clinical trial for a large number of users, and nonlinear data analysis is conducted through the machine learning based on supervised learning using the built database, whereby the quantitative associative map of the VR human factor parameters and the VR cyber sickness symptoms may be acquired for the VR user.

In addition, according to this disclosure, a function of controlling VR cyber sickness/fatigue by controlling human factor parameters may be implemented using a user-friendly intuitive interface on the GUI including as a parameter control button and a VR cyber sickness indication button in the VR contents creation and editing step.

In addition, according to this disclosure, it is possible to implement a SW tool that may control in advance in such a manner as to quantify the VR cyber sickness/fatigue in offline when manufacturing the VR application contents. In addition, the existing commercial VR game engine (Unity, Unreal, etc.) may be implemented as a stand-alone human factor based VR content authoring tool for plug-in type or general independent VR application content.

In addition, this disclosure may be used for the development of VR guidelines to best practices in industry for manufacturing the VR applications with the VR cyber sickness/fatigue being alleviated.

Meanwhile, according to an aspect of this disclosure, it is possible to provide software or a computer-readable medium having executable instructions for performing the operation method of the VR sickness prediction model generating apparatus may be provided. The executable instructions may include those of displaying virtual reality content on a display unit, detecting first VR sickness information of a user who experiences the virtual reality content using a sensor, determining second VR sickness information using a user input that is input from the user in response to a request for inputting a degree of VR sickness for the virtual reality content, performing machine learning based on supervised learning using VR sickness-inducing factors for the virtual reality content, the first VR sickness information, and the second VR sickness information, and determining a correlation between the VR sickness-inducing factors and a list of VR sickness symptoms on a basis of the performed machine learning.

Although exemplary methods of the present disclosure are described as a series of operation steps for clarity of a description, the present disclosure is not limited to the sequence or order of the operation steps described above. The operation steps may be simultaneously performed, or may be performed sequentially but in different order. In order to implement the method of the present disclosure, additional operation steps may be added and/or existing operation steps may be eliminated or substituted.

Various embodiments of the present disclosure are not presented to describe all of available combinations but are presented to describe only representative combinations. Steps or elements in various embodiments may be separately used or may be used in combination.

In addition, various embodiments of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various embodiments to be executed in an apparatus or on a computer, and a non-transitory computer-readable medium storing such software or machine-executable instructions so that the software or instructions can be executed in an apparatus or on a computer.

The invention claimed is:

1. A method of generating a VR sickness prediction model, the method comprising:
   displaying virtual reality content on a display unit;
   detecting first VR sickness information of a user who experiences the virtual reality content using a sensor, the first VR sickness information including a change in at least one of a posture, a facial expression, a gesture, and a voice of the user;
   determining second VR sickness information using a user input that is input from the user in response to a request for inputting a degree of VR sickness for the virtual reality content;
   performing machine learning based on supervised learning using VR sickness-inducing factors for the virtual reality content, the first VR sickness information, and the second VR sickness information; and
   determining a correlation between the VR sickness-inducing factors and a list of VR sickness symptoms on a basis of the performed machine learning,
   wherein the VR sickness-inducing factors of the virtual reality content includes at least one of binocular parallax and depth of field,
   wherein the determining of the correlation between the VR sickness-inducing factors and the list of VR sickness symptoms includes:
   determining a quantitative correlation between the VR sickness-inducing factors and the list of VR sickness symptoms, by causing at least one of items in the list of VR sickness symptoms to be gradually changed in magnitude as the VR sickness-inducing factors for the virtual reality content change, and
   wherein the performing of the machine learning based on supervised learning includes:
   determining a feature vector acquired using the first VR sickness information as data in the machine learning based on supervised learning;
   determining the second VR sickness information as a label for the data in the machine learning based on supervised learning; and
   performing the machine learning based on supervised learning using the data and the label for the data.

2. The method according to claim 1, wherein the list of VR sickness symptoms includes at least one of discomfort, fatigue, headache, eye fatigue, difficulties with focusing, sweating, nausea, difficulties with attention, brain fog, visual acuity, dizziness, hallucinations, stomachache, cyber sickness, burping, and other symptoms.

3. The method according to claim 2, wherein the sensor includes at least one of an image capturing sensor and a biological signal detection sensor;
   the first VR sickness information is at least one of an image of the user acquired from the image capturing sensor and a magnitude of biological signal of the user acquired from the biological signal detection sensor; and
   the second VR sickness information is a degree of at least one of the items in the list of VR sickness symptoms input from the user in response to the request for inputting the degree of the VR sickness for the virtual reality content.

4. The method according to claim 1, further comprising:
   displaying the correlation between the determined VR sickness-inducing factors and the list of VR sickness symptoms on a display unit using a graphical user interface GUI.

5. The method according to claim 1, further comprising:
   predicting the correlation between the VR sickness-inducing factors and the list of VR sickness symptoms for given virtual reality content on a basis of the performed machine learning.

6. An apparatus for generating a VR sickness prediction model, the apparatus comprising:
   a display unit displaying virtual reality content;
   a user input unit; and
   a control unit detecting first VR sickness information of a user who experiences the virtual reality content using a sensor, determining second VR sickness information using a user input that is input from the user in response to a request for inputting a degree of VR sickness for the virtual reality content, performing machine learning based on supervised learning using VR sickness-inducing factors for the virtual reality content, the first VR sickness information, and the second VR sickness information, and determining a correlation between the VR sickness-inducing factors and a list of VR sickness symptoms on a basis of the performed machine learning,
   wherein the first VR sickness information includes a change in at least one of a posture, a facial expression, a gesture, and a voice of the user, and
   wherein the VR sickness-inducing factors of the virtual reality content includes at least one of binocular parallax and depth of field,
   wherein the control unit determines a quantitative correlation between the VR sickness-inducing factors and the list of VR sickness symptoms, by causing at least one of items in the list of VR sickness symptoms to be gradually changed in magnitude as the VR sickness-inducing factors for the virtual reality content change, and
   wherein the control unit determines a feature vector acquired using the first VR sickness information as data in the machine learning based on supervised learning, determines the second VR sickness information as a label for the data in the machine learning based on supervised learning, and performs the machine learning based on supervised learning using the data and the label for the data.

7. The apparatus according to claim 6, wherein the list of VR sickness symptoms includes at least one of discomfort, fatigue, headache, eye fatigue, difficulties with focusing, sweating, nausea, difficulties with attention, brain fog, visual acuity, dizziness, hallucinations, stomachache, cyber sickness, burping, and other symptoms.

8. The apparatus according to claim 7, wherein the sensor includes at least one of an image capturing sensor and a biological signal detection sensor;
   the first VR sickness information is at least one of an image of the user acquired from the image capturing sensor and a magnitude of biological signal of the user acquired from the biological signal detection sensor; and
   the second VR sickness information is a degree of at least one of the items in the list of VR sickness symptoms input from the user in response to the request for inputting the degree of the VR sickness for the virtual reality content.

9. The apparatus according to claim 6, wherein the control unit displays the correlation between the determined VR sickness-inducing factors and the list of VR sickness symptoms on a display unit using a graphical user interface GUI.

10. The apparatus according to claim 6, wherein the control unit predicts the correlation between the VR sickness-inducing factors and the list of VR sickness symptoms for given virtual reality content on a basis of the performed machine learning.

* * * * *